(12) United States Patent
Holsten

(10) Patent No.: US 8,529,599 B2
(45) Date of Patent: Sep. 10, 2013

(54) TISSUE TENSION DETECTION SYSTEM

(75) Inventor: Henry E. Holsten, Covington, GA (US)

(73) Assignee: Covidien LP, Mansfield, MA (US)

( * ) Notice: Subject to any disclaimer, the term of this patent is extended or adjusted under 35 U.S.C. 154(b) by 535 days.

(21) Appl. No.: 12/857,803

(22) Filed: Aug. 17, 2010

(65) Prior Publication Data

US 2010/0312146 A1 Dec. 9, 2010

Related U.S. Application Data

(63) Continuation of application No. 11/446,646, filed on Jun. 5, 2006.

(60) Provisional application No. 60/687,214, filed on Jun. 3, 2005.

(51) Int. Cl.
*A61B 17/068* (2006.01)

(52) U.S. Cl.
USPC ............... 606/219; 227/175.1; 600/587

(58) Field of Classification Search
USPC ............. 600/587, 561; 606/219; 227/175.1
See application file for complete search history.

(56) References Cited

U.S. PATENT DOCUMENTS

| | | | |
|---|---|---|---|
| 4,204,544 A | 5/1980 | Feldstein et al. | |
| 4,206,980 A | 6/1980 | Krueger et al. | |
| 4,294,015 A | 10/1981 | Drouin et al. | |
| 4,319,236 A | 3/1982 | Brace et al. | |
| 4,473,077 A | 9/1984 | Noiles | |
| 4,576,167 A | 3/1986 | Noiles | |
| 4,646,745 A | 3/1987 | Noiles | |
| 4,813,435 A | 3/1989 | Arms | |
| 4,993,428 A | 2/1991 | Arms | |
| 5,005,749 A | 4/1991 | Aranyi | |
| 5,016,479 A | 5/1991 | Taback | |
| 5,071,420 A | 12/1991 | Paulos et al. | |
| 5,083,573 A | 1/1992 | Arms | |
| 5,119,983 A | 6/1992 | Green et al. | |
| 5,306,979 A | 4/1994 | Schwarz, Jr. | |
| 5,526,820 A * | 6/1996 | Khoury | 600/561 |
| 5,588,579 A | 12/1996 | Schnut et al. | |
| 5,605,035 A | 2/1997 | Pethrick et al. | |
| 5,722,419 A | 3/1998 | Semmlow et al. | |
| 5,895,413 A | 4/1999 | Nordstrom | |
| 5,915,616 A * | 6/1999 | Viola et al. | 227/179.1 |
| 6,053,390 A | 4/2000 | Green et al. | |
| 2001/0018095 A1 | 8/2001 | Shlenker et al. | |
| 2002/0099315 A1 | 7/2002 | Lebner | |

(Continued)

FOREIGN PATENT DOCUMENTS

WO    WO 03/090630 A1 *  4/2003

*Primary Examiner* — Sean Dougherty
*Assistant Examiner* — Michael C Stout

(57) ABSTRACT

An apparatus for indicating the amount of tension applied to separate internal organ sections includes a housing, a shaft extending from the housing, and a fastener applier. The fastener applier is supported on the shaft. The fastener applier includes an anvil assembly and a cartridge assembly. The anvil assembly is positionable between first and second positions relative to the cartridge assembly. The anvil assembly and the cartridge assembly include a tissue detection device positioned to contact separate internal organ sections to generate a signal indicative of an amount of tension between the organ sections as the anvil assembly moves between the first and second positions. The tissue detection device is operably coupled to a gauge configured and dimensioned to generate an output based upon the signal. The output indicates the amount of tension between the organ sections.

18 Claims, 4 Drawing Sheets

(56) References Cited

U.S. PATENT DOCUMENTS

| | | |
|---|---|---|
| 2002/0143275 A1* | 10/2002 | Sarvazyan et al. ............ 600/587 |
| 2003/0021903 A1 | 1/2003 | Shlenker et al. |
| 2004/0010276 A1 | 1/2004 | Jacobs et al. |
| 2004/0148020 A1 | 7/2004 | Vidlund et al. |
| 2005/0006433 A1* | 1/2005 | Milliman et al. .......... 227/176.1 |
| 2005/0080454 A1 | 4/2005 | Drews et al. |
| 2005/0131390 A1* | 6/2005 | Heinrich et al. .................. 606/1 |
| 2006/0068168 A1 | 3/2006 | Olson et al. |
| 2006/0094318 A1 | 5/2006 | Matsuda et al. |

* cited by examiner

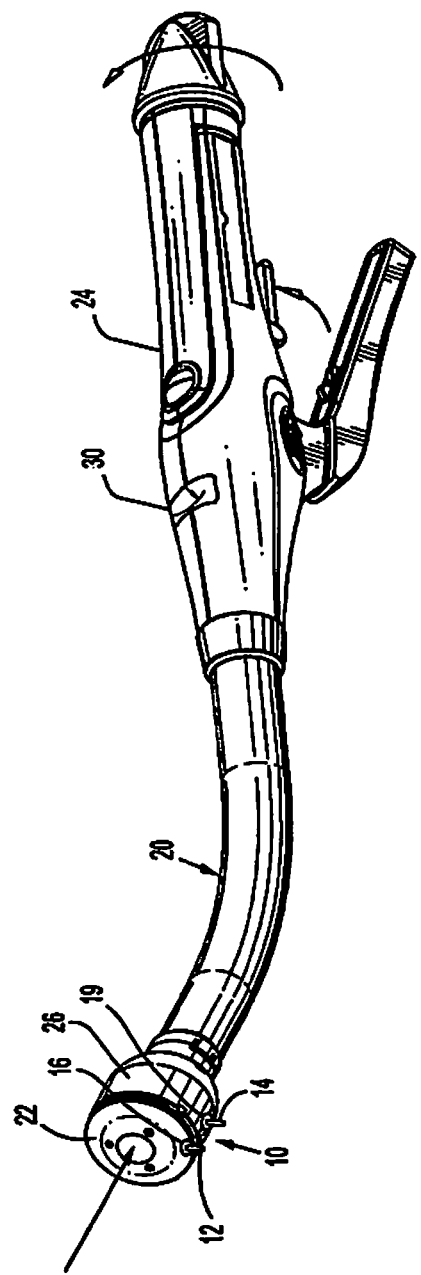
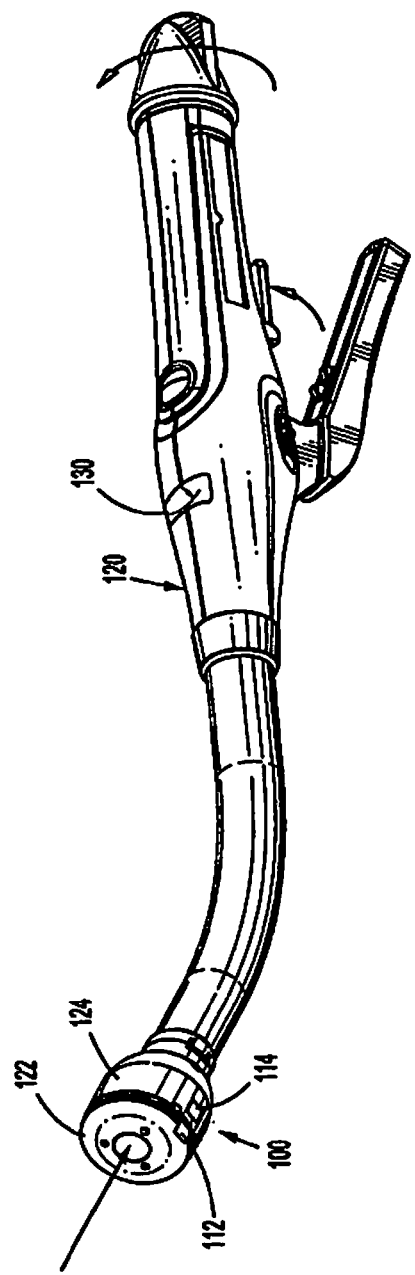
FIG. 1
FIG. 2

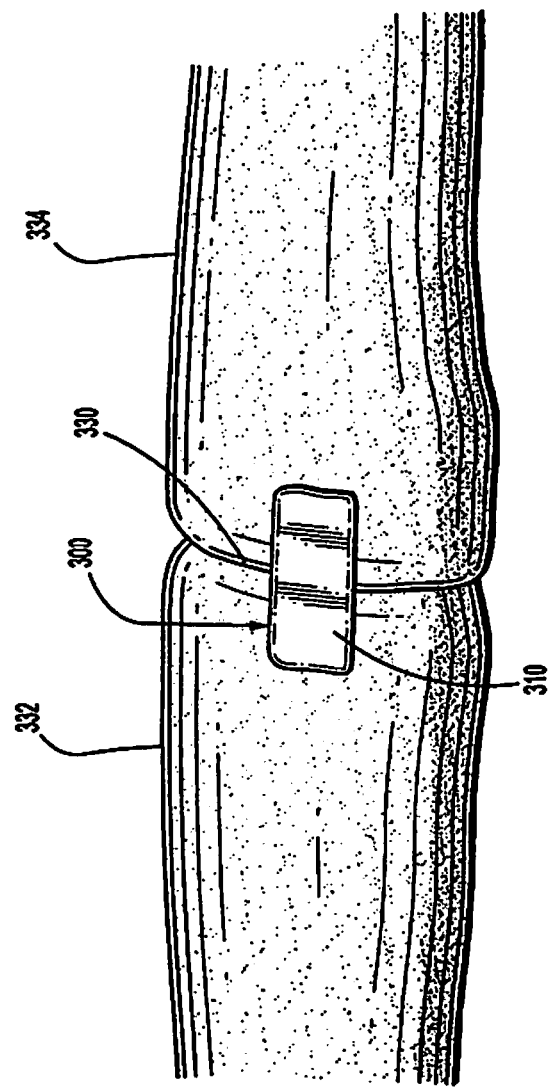

TISSUE TENSION DETECTION SYSTEM

CROSS-REFERENCE TO RELATED APPLICATIONS

This application is a continuation of U.S. patent application Ser. No. 11/446,646, filed on Jun. 5, 2006, which claims priority to, and the benefit of, U.S. Provisional Patent Application Ser. No. 60/687,214, filed Jun. 3, 2005, the entire disclosures of which are incorporated by reference herein.

BACKGROUND

1. Technical Field

The present disclosure relates to a method and/or apparatus for measuring the tension in body tissue. More particularly, the present disclosure relates to a method and/or apparatus for measuring the tension in body tissue at a site of a surgical anastomosis.

2. Background of Related Art

Anastomosis is the surgical joining of separate hollow organ sections. Typically, an anastomosis procedure follows a surgical procedure in which a diseased or defective section of hollow tissue is removed and the remaining end sections are drawn together and joined. Depending on the desired anastomosis procedure, the end sections may be joined by either circular, end-to-end, or side-to-side organ reconstruction methods.

In a known circular anastomosis procedure, two ends of organ sections are drawn together and joined by means of a stapling device which drives a circular array of staples through the end of each organ section and simultaneously cores any tissue interior of the driven circular array of staples to free a tubular passage. Examples of devices for performing circular anastomosis of hollow organs are described in U.S. Pat. Nos. 6,053,390; 5,588,579; 5,119,983; 5,005,749; 4,646,745; 4,576,167; and 4,473,077, each of which is incorporated herein in its entirety by reference. Typically, these devices include an elongated shaft having a handle portion at a proximal end thereof to effect actuation of the device and a staple holding component disposed at a distal end thereof. An anvil assembly including an anvil shaft with attached anvil head is mounted to the distal end of the device such that the anvil head is movable towards the staple holding component. The two ends of the organ sections are drawn together and clamped between the anvil head and the staple holding component of the device by securing one end of the organ section to the anvil assembly, securing the other end of the organ section about the staple holding component, and moving the anvil head towards the staple holding component. The clamped tissue is stapled by driving one or more staples from the staple holding component so that the ends of the staples pass through the organ sections and are deformed by the anvil head. An annular knife is concurrently advanced to core tissue within the hollow organ to free a tubular passage within the organ. Typically, this procedure is conducted endoscopically or laparoscopically using endoscopic instruments.

Although the circular anastomosis procedure described above has provided substantial improvements to surgical procedures requiring anastomosis, additional improvements are desired. For example, when the two ends of the organ sections to be anastomosed are drawn together, tension is generated in the organ sections. Because of the type of surgery, it can be difficult for a surgeon to determine how much tension is being or has been applied to the organ sections at the anastomotic site. Excessive tension on the organ sections at the anastomotic site may result in complications, e.g., strictures, postoperative leaks, necrosis, etc.

Accordingly, it would be desirable to provide a surgical apparatus and/or method for measuring the tissue tension at an anastomotic site and providing a surgeon with immediate data indicating the magnitude of the tension. It would also be desirable to provide an apparatus which is suitable for use with a circular anastomosis device and could measure the initial and residual tension at an anastomotic site during a surgical procedure.

SUMMARY

The present disclosure is directed to an apparatus for indicating the amount of tension applied to separate internal organ sections. The apparatus includes a housing, a shaft extending from the housing, and a fastener applier. The fastener applier is supported on the shaft. The fastener applier includes an anvil assembly and a cartridge assembly. The anvil assembly is positionable between first and second positions relative to the cartridge assembly. The anvil assembly moves a first organ section towards a second organ section as the anvil assembly moves between the first and second positions such that an amount of tension is generated between the first and second organ sections. In the first position, the anvil assembly is spaced apart from the cartridge assembly, and in the second position, the anvil assembly is in close cooperative alignment with cartridge assembly.

The anvil assembly and the cartridge assembly include a tissue detection device positioned to contact separate internal organ sections to generate a signal indicative of an amount of tension between the organ sections as the anvil assembly moves between the first and second positions. The tissue detection device is operably coupled to a gauge configured and dimensioned to generate an output based upon the signal. The output indicates the amount of tension between the organ sections.

In embodiments, the tension detection device includes a pair of contacts. One or more contacts are positioned to extend through one or more openings formed in one or both of the anvil assembly and the cartridge assembly. One or more contacts may be movable between extended and retracted positions. One or more contacts may extend or retract from the one or more openings in response to movement of the anvil assembly between the first and second positions. The housing may include a switch that extends and retracts the one or more contacts upon the actuation of the switch. One or more of the contacts may be connected to the gauge by one or more wires.

In embodiments, the gauge may be supported within the fastener applier. The gauge may be a strain gauge. The gauge may be operably coupled to an indicator supported on the housing that displays the output. In embodiments the indicator displays the output in real time.

According to one aspect, the present disclosure is directed to a method for detecting an amount of tension applied to organ sections and includes the step of providing an apparatus including a housing, a shaft extending from the housing, and a fastener applier. The fastener applier is supported on the shaft and includes an anvil assembly and a cartridge assembly having a tissue detection device. The tissue detection device is operably coupled to a gauge. The method includes the steps of positioning the anvil assembly between first and second positions relative to the cartridge assembly such that a first organ section moves towards a second organ section; applying tension to the organ sections; and generating an output that indicates an amount of tension between the organ sections. The method may include the steps of causing the tissue tension device to generate a signal indicative of the amount of tension between the organ sections and causing the gauge to generate the output based upon the signal. One step may include causing an indicator that is operably coupled to the gauge to display the output. In one embodiment, the tissue detection device includes a pair of contacts such that the method involves moving one or more of the contacts in response to movement of the anvil assembly between the first and second positions. One step may include moving one or more of the contacts between extended and retracted positions relative to one or both of the anvil assembly and the cartridge assembly.

BRIEF DESCRIPTION OF THE DRAWINGS

Embodiments of the presently disclosed apparatus are described herein with reference to the drawings, wherein:

FIG. 1 is a front perspective view of an embodiment of the presently disclosed apparatus;

FIG. 2 is a front perspective view of an alternate embodiment of the presently disclosed apparatus;

FIG. 4 is a side view of a further embodiment of the presently disclosed apparatus located at an anastomotic site between two organ sections with no tension applied to the organ sections.

DETAILED DESCRIPTION OF EMBODIMENTS

Figure 3:
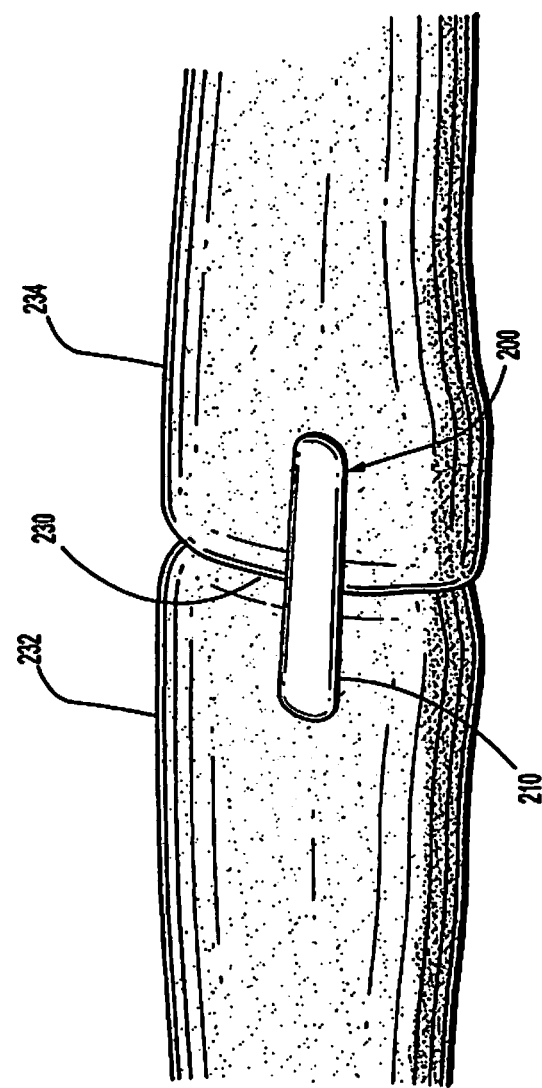
FIG. 3 is a side view of another embodiment of the presently disclosed apparatus located at an anastomotic site between two organ sections.

Embodiments of the presently disclosed method and apparatus for measuring tissue tension at an anastomotic site will now be described in detail with reference to the drawings wherein like numerals designate identical or corresponding elements in each of the several views. As is common in the surgical apparatus art, the term proximal will refer to a location on the device closer to the operator of the device, e.g., surgeon, while the term distal will refer to a location on the device further away from the operator of the device.

FIG. 1 illustrates one embodiment of the presently disclosed apparatus for measuring tissue tension at an anastomotic site shown generally as 10. Apparatus 10 is supported on a circular anastomosis fastener applier shown generally as 20. Apparatus 10 includes a pair of contacts or leads 12 and 14 which are positioned at a distal end of circular anastomosis fastener applier 10. Contact 12 includes a first end positioned to extend through an opening 16 formed in an anvil assembly 22 of fastener applier 20. A second end of contact 12 communicates with a tension gauge (not shown), e.g., strain gauge, supported within housing 24 of fastener applier 10. Contact 14 includes a first end positioned to extend through an opening 19 defined in a staple holding component or staple cartridge 26 of fastener applier 20. A second end of contact 14 communicates with the tension gauge in housing 24 (not shown). Contacts 12 and 14 are positioned to contact each organ section adjacent the anastomotic site to supply a signal indicative of the magnitude of tissue tension to the tension gauge. The tension gauge translates the signal sent by contacts 12 and 14 into data identifying the magnitude of tension in the organ sections. Contacts 12 and 14 can be connected to the tension gauge by wires or the like. In one embodiment, a tension indicator 30 is supported on housing 24. Tension indicator 30 communicates with the tension gauge to display in real time the tension in the organ sections. It is envisioned that fastener applier 20 may include a part which is connectable to a strain gauge and indicator which are located externally of housing 24.

During an anastomotic procedure, anvil assembly 22 is repositioned towards staple cartridge 26 and moves a first organ section towards a second organ section, thereby applying an amount of tension to the organ sections. Anvil assembly 22 is repositionable, in relation to staple cartridge 26, throughout a plurality of positions including a first position that is spaced apart from staple cartridge 26 and a second position that is in close cooperative alignment with the staple cartridge 26.

In one embodiment, contacts 12 and 14 are retractable into and out of openings 16 and 19, wherein contacts 12, 14 are repositionable between an extended position and a retracted position. In one embodiment, contacts 12 and 14 are extended from openings 16 and 19 in response to approximation of the anvil assembly 22 and staple holding component 24. Alternatively, a manual switch may be provided to extend the contacts.

FIG. 2 illustrates an alternate embodiment of the presently disclosed apparatus for measuring tissue tension at an anastomotic site shown generally as 100. Apparatus 100 is similar to apparatus 10 in that apparatus 100 includes a first contact 112 mounted on an anvil assembly 122 of fastener applier 120 and a second contact 114 mounted on a staple holding component or staple cartridge 124 of fastener applier 120. However, contacts 112 and 114 are flat contacts which are mounted on an outer rim of both anvil assembly 122 and staple holding component 124 at a position to contact organ sections at a location adjacent the anastomotic site. Each contact 112 and 114 communicates with a tension gauge (not shown) supported within fastener applier 120 which communicates with a tension indicator 130 as discussed above with respect to apparatus 10. As discussed above, it is envisioned that the tension gauge and indicator may be located externally of the fastener applier.

In a further embodiment, tension indicators 30, 130 may include an audible and/or visual alarm indicator (i.e. red light, buzzer, horn, bell, etc.) that informs the operator that a predetermined amount of tension is being applied to the organ sections. The setting for the alarm indicator is operator adjustable and the procedure to be performed is one of several criteria that is considered when establishing the predetermined amount of tension for the alarm setting.

FIG. 3 illustrates another embodiment of the presently disclosed apparatus for measuring tissue tension shown generally as 200 which is separate from a fastener applier. Apparatus 200 can be applied across an anastomotic site 230 to produce a reference indication of the magnitude of the tension where the organ sections are joined. Apparatus 200 includes an elongated member 210 formed of a material which bridges anastomotic site 230 and is, in one embodiment, initially slack. When excess tension exists in the anastomosed tissue, the material goes taut or releases from the tissue. In another embodiment, member 210 is secured to organ sections 232 and 234 using an adhesive or the like. Member 210 can be monitored endoscopically using an endoscope or other viewing equipment. Although apparatus 200 is illustrated as a strip of material, it is also contemplated that apparatus 200 may be a suture or any other material for maintaining the two sections of the anastomotic site in close approximation. It is further contemplated that apparatus 200 may be formed of a biocompatible and/or bioabsorbable material.

Figure 4A:
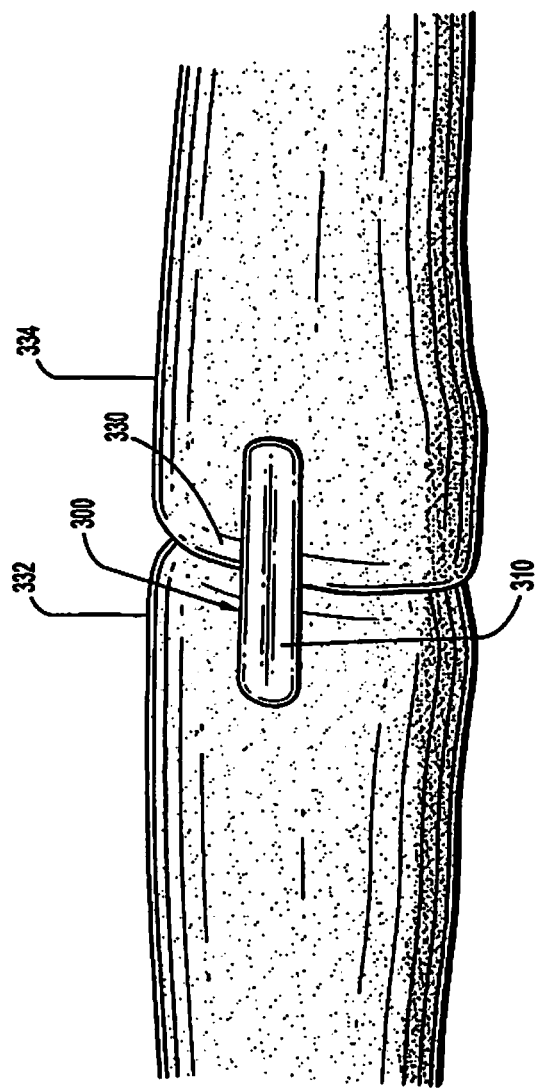
FIG. 4A is a side view of the apparatus of FIG. 4 with tension applied to the organ sections.

In another embodiment shown in FIG. 4, device 300 is formed of a body of material 310 which can be visualized via x-ray, MRI, CT scan, ultrasound or any other known device. Body of material 310 is positioned to bridge an anastomotic site 330. In one embodiment, when excess tension is present in the tissue or organ sections 332 and 334, body 310 undergoes a physical change to indicate excess tension at anastomotic site 330, e.g., body 310 may be stretched (see FIG. 4A), such that the change in the width and/or length of body 310 is indicative of the change in tension applied to organ sections 332 and 334. Further still, changes to the thickness of body 310 indicate the change in tension applied to organ sections 332 and 334. It is envisioned that other changes may occur upon application of tension to body 310, e.g., a color change may occur from a bioabsorbable marker, or a release from the organ sections may indicate a change in tension, etc.

The embodiments illustrated in FIGS. 3-4A are configured for measuring the tension applied to organ sections 232 and 234 or 332, 334 prior to approximation of the organ sections with a surgical stapling apparatus as well as during approximation and subsequent to the approximation. Further still, the disclosed embodiments are capable of measuring and indicating the amount of tension applied to the organ sections before, during, and after the firing of surgical staples from the surgical stapling apparatus. It is contemplated that devices 200, 300 may be formed from an elastic material as well as non-elastic materials.

In one embodiment, device 200 (FIG. 3) is attached to organ sections 232, 234 prior to approximation of organ sections 232, 234. This occurs after a section of the subject organ is removed between organ sections 232, 234. Device 200 is attached using known endoscopic techniques through an access port (e.g. cannula) (not shown). Once attached, device 200 may be monitored through the access port using an endoscope (not shown). As organ sections 232, 234 are approximated using a circular anastomosis fastener (i.e. apparatus 10 as shown in FIG. 1) tension is applied to organ sections 232, 234. If the applied tension exceeds a predetermined amount, device 200 may detach at one or both attachment points or have a certain amount of slack between the attachment points. Specifically, once device 200 is attached to the spaced apart organ sections 232, 234, movement of the organ sections towards one another (i.e. approximation) reduces the tension applied to device 200 and causes it to sag or go slack, whereupon, device 200 may detach from one or both of its attachment points.

In an alternate embodiment, device 200 is attached as described hereinabove to organ sections 232, 234 after approximation, but prior to joining organ sections 232, 234. In this configuration, the practitioner observes device 200 as before. If the tension applied to organ sections 232, 234 exceeds a predetermined amount during the joining of the sections, device 200 may detach from one or both of the organ sections or go slack, as discussed hereinabove.

In a further embodiment, device 200 is attached as discussed hereinabove to organ sections 232, 234 after organ sections 232, 234 are anastomosed. In this configuration, device 200 is observed as before, wherein tension in the anastomosed organ sections 232, 234 will create tension in the attached device 200. If the tension exceeds a predetermined amount, device 200 may stretch and/or deform, thereby indicating an excess tension condition. Alternatively, device 200 may include a sac of ink or dye that is released upon exceeding a predetermined amount of tension.

In another embodiment, a marker which reacts to strain or tension is applied to one or both of the organ sections to be joined. The marker can be an ink, polymer, or the like. When excess tension or any strain exists in the tissue sections, the marker reacts to the strain to provide an indication or reference of magnitude. The marker's reaction to the amount of tension applied to the organ sections may include changes in the marker's physical dimensions, a change in the marker's color, a reduction in an amount of slack in the marker, or separation of one end of the marker from an organ section. In addition, markers or devices 200, 300 may include a container (e.g. a pouch or a sac) that is embedded in marker 200, 300 such that an indicator (e.g. an ink or a dye) stored in the container is released when the tension applied to the organ sections exceeds a predetermined value.

In yet another embodiment, an electromechanical device may be operatively connected across the anastomotic site. The electromechanical device is configured to provide an output which provides an indication or measurement of tension at the site.

It will be understood that various modifications may be made to the embodiments disclosed herein. Thus, the above description should not be construed as limiting, but merely as illustrative of the disclosed apparatus and method. Those skilled in the art will envision other modifications within the scope and spirit of the claims appended hereto.

What is claimed is:

1. An apparatus for indicating the amount of tension applied to separate internal organ sections comprising:
   a housing;
   a shaft extending from the housing; and
   a fastener applier supported on the shaft, the fastener applier including an anvil assembly and a cartridge assembly, the anvil assembly being positionable between first and second positions relative to the cartridge assembly, the anvil assembly and the cartridge assembly including a tissue detection device positioned to contact separate internal organ sections to generate a signal indicative of an amount of tension between the organ sections as the anvil assembly moves between the first and second positions, the tissue detection device being operably coupled to a gauge configured and dimensioned to generate an output based upon the signal, the output indicating the amount of tension between the organ sections, the tissue detection device including a contact supported on one of the anvil assembly and the cartridge assembly, the contact being selectively movable relative to the respective anvil or cartridge assembly upon which the contact is supported.

2. The apparatus according to claim 1, wherein the tension detection device includes a first contact supported on the anvil assembly and a second contact supported on the cartridge assembly, the first contact being selectively movable relative to the anvil assembly and the second contact being selectively movable relative to the cartridge assembly.

3. The apparatus according to claim 1, wherein the contact is positioned to extend through at least one opening formed in one of the anvil assembly and the cartridge assembly.

4. The apparatus according to claim 1, wherein the shaft defines a longitudinal axis that extends distally through the shaft, wherein the contact is selectively movable between extended and retracted positions in a direction substantially transverse to the longitudinal axis.

5. The apparatus according to claim 4, wherein the contact extends or retracts through the at least one opening in response to movement of the anvil assembly between the first and second positions.

6. The apparatus according to claim 1, wherein the housing includes a switch that extends and retracts the contact upon the actuation of the switch.

7. The apparatus according to claim 1, wherein the contact is connected to the gauge by at least one wire.

8. The apparatus according to claim 1, wherein the anvil assembly is configured to move a first organ section towards a second organ section as the anvil assembly moves between the first and second positions such that an amount of tension is generated between the first and second organ sections.

9. The apparatus according to claim 1, wherein in the first position, the anvil assembly is spaced apart from the cartridge assembly, and in the second position, the anvil assembly is in close cooperative alignment with cartridge assembly.

10. The apparatus according to claim 1, wherein the gauge is supported within the fastener applier.

11. The apparatus according to claim 1, wherein the gauge is a strain gauge.

12. The apparatus according to claim 1, wherein the gauge is operably coupled to an indicator supported on the housing, the indicator displaying the output.

13. The apparatus according to claim 12, wherein the indicator displays the output in real time.

14. A method for detecting an amount of tension applied to organ sections, comprising the steps of:
   providing an apparatus including:
      a housing;
      a shaft extending from the housing; and
      a fastener applier supported on the shaft, the fastener applier including an anvil assembly and a cartridge assembly having a tissue detection device, the tissue detection device being operably coupled to a gauge;
   selectively moving a contact supported on one of the anvil assembly and the cartridge assembly relative to the respective anvil assembly or cartridge assembly upon which the contact is supported;
   positioning the anvil assembly between first and second positions relative to the cartridge assembly such that a first organ section moves towards a second organ section;
   applying tension to the organ sections; and
   generating an output that indicates an amount of tension between the organ sections.

15. The method according to claim 14, further comprising the step of:
   causing the tissue tension device to generate a signal indicative of the amount of tension between the organ sections; and
   causing the gauge to generate the output based upon the signal.

16. The method according to claim 15, further comprising the step of:
   causing an indicator that is operably coupled to the gauge to display the output.

17. The method according to claim 14, wherein the tissue detection device includes a pair of contacts, the method further comprising the step of: moving at least one of the contacts in response to movement of the anvil assembly between the first and second positions.

18. The method according to claim 17, further comprising the step of moving at least one of the contacts between extended and retracted positions relative to at least one of the anvil assembly and the cartridge assembly.

\* \* \* \* \*